United States Patent [19]

Brahler

[11] Patent Number: 5,209,658

[45] Date of Patent: May 11, 1993

[54] DENTAL PROPHY ANGLE

[75] Inventor: George R. Brahler, Lawrence, Kans.

[73] Assignee: Brahler Products, Inc., Lawrence, Kans.

[21] Appl. No.: 912,494

[22] Filed: Jul. 13, 1992

[51] Int. Cl.$^5$ .................................................. A61C 3/06
[52] U.S. Cl. ....................................... 433/125; 433/115
[58] Field of Search ................................. 433/115, 125

[56] References Cited

U.S. PATENT DOCUMENTS

| 3,740,853 | 7/1973 | Brahler | 433/125 |
| 4,266,933 | 5/1981 | Warden et al. | 433/125 |
| 4,486,175 | 12/1984 | Fisher et al. | 433/115 |
| 5,020,994 | 6/1991 | Huang | 433/125 |

Primary Examiner—John J. Wilson
Attorney, Agent, or Firm—Hovey, Williams, Timmons & Collins

[57] ABSTRACT

A disposable dental prophy angle designed to be coupled with a conventional dental tool power source, the angle being used in dental prophylaxis. The dental prophy angle is fabricated from synthetic resin material and comprises a housing presenting a head end and a shank end with a passageway extending between said ends, a drive shaft extending along the passageway, a plurality of sealing rings integrally formed as part of the housing and extending inwardly therefrom into sealing engagement with the drive shaft, and a pair of auger flights integrally formed as part of the shaft for propelling buccal matter along the passageway for ejection through the head end.

13 Claims, 1 Drawing Sheet

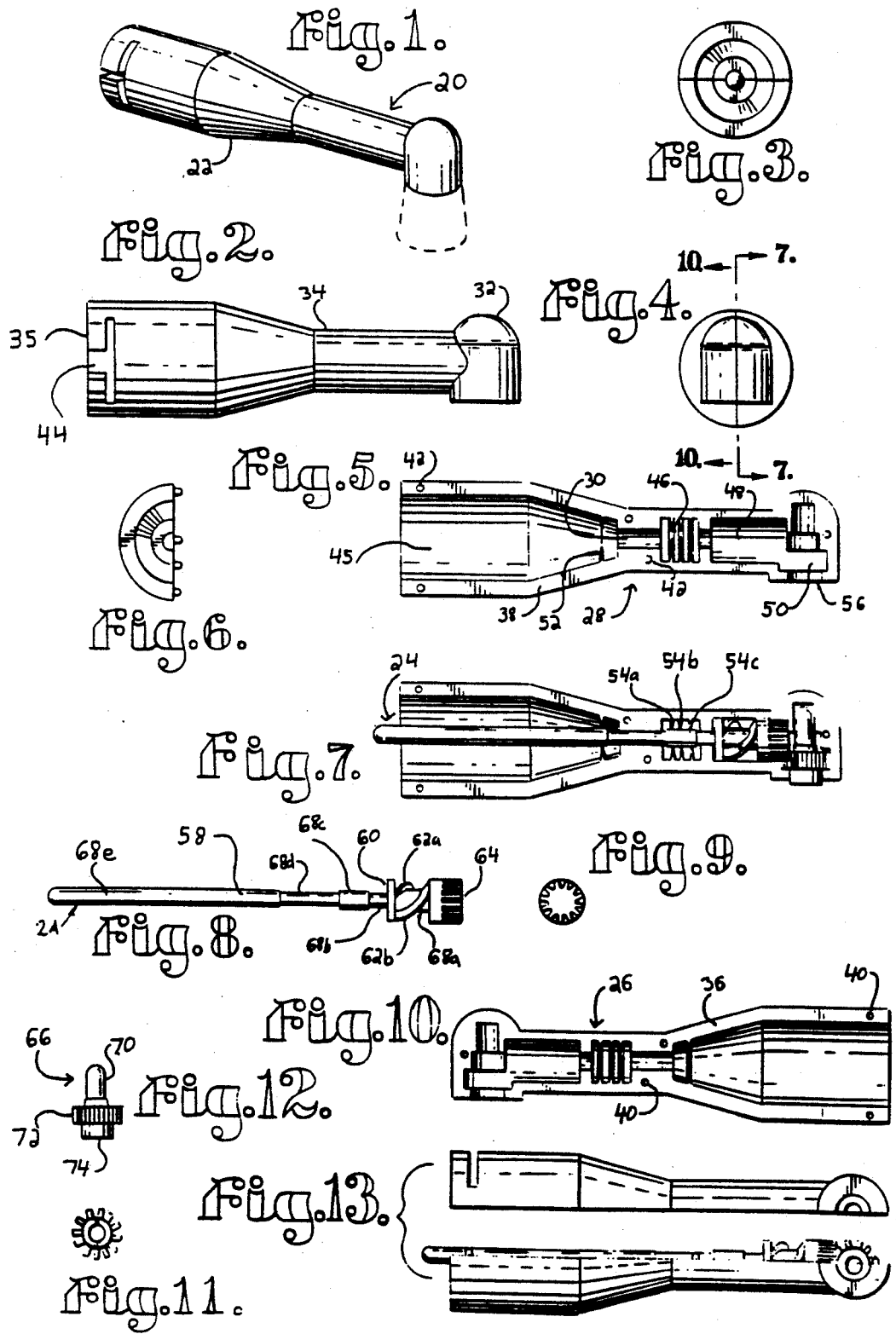

DENTAL PROPHY ANGLE

BACKGROUND OF THE INVENTION

1. Field of the Invention

The present invention is concerned with the field of dentistry and specifically with the field of dental prophy angles used for dental prophylaxis. More particularly, the invention is concerned with a dental prophy angle including a housing presenting a head end and a shank end with a passageway extending between said ends, a drive shaft extending along the passageway, a plurality of sealing rings integrally formed as part of the housing and extending inwardly therefrom into sealing engagement with the drive shaft, and a pair of auger flights integrally formed as part of the shaft for propelling buccal matter along the passageway for ejection through the head end.

2. Description of The Prior Art

In recent years, concern for preventing the transmission of diseases during dental procedures has increased. One possible transmission path for diseases is improperly sterilized dental equipment.

Disposable dental prophy angles provide a conventional solution to the problems of reusable dental equipment. Disposable prophy angles are generally formed of a suitable synthetic resin material and are designed to be coupled with a conventional dental power supply.

Disposable prophy angles effectively prevent the spread of disease from patient to patient, but do not completely protect the dentist. Buccal matter such as saliva, blood, and tissue particles can migrate from the patient's mouth to the dentist's handset through the passageways of dental prophy angles. Thus, the prior art points out the need for an improved disposable prophy angle that can prevent the migration of buccal matter from the patient's mouth to the dentist.

SUMMARY OF THE INVENTION

The present invention solves the prior art problems discussed above and provides a distinct advance in the state of the art. More particularly, the prophy angle of the present invention prevents the migration of buccal matter from the patient's mouth to the dentist's handpiece.

The preferred dental prophy angle includes a housing presenting a head end and a shank end with a passageway extending between said ends, a drive shaft extending along the passageway, and means for preventing the migration of buccal matter from the head end to the shank end. In preferred forms, a pair of auger flights, integrally formed as part of the drive shaft, propel any buccal matter present in the passageway toward the head end of the prophy angle for ejection therethrough. In particularly preferred forms, the prophy angle also includes a plurality of sealing rings integrally formed as part of the housing and extending inwardly therefrom into sealing engagement with the drive shaft.

BRIEF DESCRIPTION OF THE DRAWINGS:

FIG. 1 is a perspective view of the preferred dental prophy angle in accordance with the present invention;

FIG. 2 is a side elevational view of the prophy angle;

FIG. 3 is an end elevational view of the shank end of the prophy angle;

FIG. 4 is an end elevational view of the head end of the prophy angle;

FIG. 5 is a side elevational view of the interior of the left portion of the housing of the prophy angle;

FIG. 6 is an end elevational view of the shank end of the left portion of the housing;

FIG. 7 is a sectional view of the prophy angle taken along line 7—7 of FIG. 4;

FIG. 8 is an elevational view of the drive shaft assembly;

FIG. 9 is an end elevational view of the forward end of the drive shaft showing the drive gear;

FIG. 10 is a sectional view taken along line 10—10 of FIG. 4;

FIG. 11 is a bottom plan view of the output component;

FIG. 12 is an elevational view of the output component; and

FIG. 13 an exploded bottom plan view of the prophy angle.

DETAILED DESCRIPTION OF THE PREFERRED EMBODIMENT

Referring now to the drawing figures, prophy angle 20 broadly includes housing 22 and drive assembly 24. Housing 22 is constructed to present left housing portion 26 and right housing portion 28 with passageway 30 extending along the length thereof between head end 32 to shank end 34. Housing portions 26 and 28 are preferably composed of synthetic resin material and are so configured for economy of manufacture.

Housing portions 26 and 28 are generally symmetrical and present respective, flat engagement surfaces 36 and 38 configured to mate with one another along the center line of prophy angle 20. Left housing portion 26 includes a plurality of outwardly extending connection pegs 40 designed for snug reception in corresponding apertures 42 defined in surface 38 of right housing portion 28 for holding housing portions 26,28 together. Left housing portion 26 also includes T-shaped expansion slot 44 defined therein adjacent shank end 34 that allows the opening 35 of said shank end to expand for receiving and holding a dental tool drive power source of slightly greater diameter than said shank end opening 35.

Passageway 30 includes power source connection chamber 45, sealing chamber 46, auger chamber 48, and output chamber 50. The interior walls defining connection chamber 45 includes sealing ring 52 extending inwardly therefrom. Similarly, the interior walls defining sealing chamber 46 include three sealing rings 54a, 54b, and 54c. Output chamber 50 extends transversely relative to auger chamber 48 and opens through head end 32 at output opening 56.

Drive assembly 24 includes drive shaft 58, positioning ring 60, auger flights 62a and 62b, drive gear 64, and output component 66. Preferably, components 58–64 are integrally formed of synthetic resin material with the relative positions as shown in FIGS. 7 and 8. More particularly, drive shaft 58 extends along passageway 30 between auger chamber 48 and connection chamber 45 with the rearward end of shaft 58 extending slightly beyond chamber 45 as illustrated in FIG. 7.

As illustrated, drive shaft 58 includes auger section 68a, first intermediate section 68b, sealing section 68c, second intermediate portion 68d, and rearward portion 68e. As illustrated, auger section 68a, sealing section 68c, and rearward portion 68e present diameters slightly greater than intermediate sections 68b,d. In this regard, auger section 68a supports integral auger flights 62a,b in auger chamber 48, the surface of sealing section 68c is engaged by sealing rings 54a,b,c, and the forward most portion of the surface of rearward portion 68e is engaged by sealing ring 52.

Positioning ring 60 extends around shaft 58 adjacent the rearward portions of auger flights 62a,b and helps maintain the axial alignment of shaft 58 within passageway 30. Output component 66 is coupled in axial alignment with the forward end of drive shaft 58 as shown.

Output component 66 is positioned within output chamber 50 with the axis thereof transverse to the axis of shaft 58. Output component 66 integrally includes alignment stub shaft 70, output gear 72 and output member 74. Stub shaft 70 along with gear 72 cooperatively maintain the transverse and axial alignment of output component 66 within chamber 50. In this position, output gear 72 engages drive gear 64 for driven rotation thereby. Output member 74 extends through output opening 56 and is configured for coupling with a dental prophylaxis workpiece such as a dental cup.

In use, a dental drive power source is inserted into shank end opening 35 and slipped over drive shaft rearward portion 68e. The power source is pressure fitted within expansion slot 44 for holding the power source engaged with shaft 58. A prophylaxis tool is then coupled with output member 74 and the power source activated to rotate drive shaft 58 which in turn rotates drive gear 64 and thereby output component 66 and the prophylaxis tool.

As those skilled in the art will appreciate, buccal matter from the dental patient's mouth may enter passageway 30 by way of output opening 56. In the prior art, such buccal matter migrates along the prophy angle passageway and out through the shank end. In so doing, this can contaminate the drive source, but additionally can expose the dentist or technician to the buccal matter. The present invention prevents this from occurring. In particular, rotation of drive shaft 58 also rotates auger flights 62a,b which propels buccal matter forward through passageway 30 and expels this buccal matter from prophy angle 20 through output opening 56. When the dental power source is turned off and auger flights 62a,b are not rotating, small amounts of buccal matter may migrate beyond flights 62a,b. This migration is prevented by sealing rings 54a,b,c engaged with shaft sealing section 68c, and by sealing ring 52 engaged with shaft rearward portion 68e.

As those skilled in the art will appreciate, the present invention encompasses many variations in the preferred embodiment described herein. For example, in some circumstances one auger flight will be sufficient and could be positioned at a different location along the prophy angle passageway. Additionally, the preferred prophy angle presents an output transverse to the long axis, which could be positioned at some other relative orientation. As a final example, a greater or lesser number of sealing rings could be provided.

Having thus described the preferred embodiment of the present invention, the following is claimed as new and desired to be secured by Letters Patent:

1. A dental prophy angle comprising:
   a housing presenting a head end and a shank end with a passageway extending through said housing between said ends;
   a drive assembly including an output member extending from said head end for coupling a dental tool thereto and including a drive shaft extending along said passageway, said passageway being subject to the entry of matter thereinto from a patient's mouth by way of said head end; and
   means for ejecting said matter from said passageway and out through said head end.

2. The prophy angle as set forth in claim 1, said ejecting means including at least one auger flight extending outwardly from said shaft and configured for propelling said matter along said passageway towards and out through said head end during shaft rotation.

3. The prophy angle as set forth in claim 2, said housing including structure defining an auger chamber adjacent to said head end, said auger flight being positioned within said auger chamber.

4. The prophy angle as set forth in claim 2, said housing presenting an inner surface, said prophy angle further including an annular sealing ring extending inwardly from said inner surface towards said shaft into a close sealing relationship therewith.

5. The prophy angle as set forth in claim 4 further including a plurality of said sealing rings.

6. The prophy angle set forth in claim 2, said ejecting means including a pair of said auger flights.

7. The prophy angle as set forth in claim 6, said auger flights being integrally formed as part of said shaft.

8. The prophy angle as set forth in claim 7, said shaft and flights being composed of synthetic resin material.

9. The prophy angle set forth in claim 1, said housing presenting an inner surface, said prophy angle further including an annular sealing ring extending inwardly from said inner surface towards said shaft into a close sealing relationship therewith.

10. The prophy angle as set forth in claim 9, said preventing means including a plurality of said sealing rings.

11. The prophy angle as set forth in claim 10, said rings being integrally formed as part of said housing.

12. The prophy angle set forth in claim 11, said rings and housing being formed of synthetic resin material.

13. The prophy angle as set forth in claim 1, said shaft presenting a forward end adjacent said housing head end, said drive assembly further including a drive gear coupled with said shaft forward end, said output member including an output gear rotatably coupled with said drive gear.

* * * * *